United States Patent [19]
Haas et al.

[11] Patent Number: 6,011,179
[45] Date of Patent: Jan. 4, 2000

[54] PROCESS FOR THE PRODUCTION OF AMINES FROM IMINES OF NITRILES

[75] Inventors: Thomas Haas, Frankfurt; Karl Ludwig Weber, Dieburg; Klaus Stadtmuller, Alzenau; Willi Hofen, Rodenbach; Rudolf Vanheertum, Kahl, all of Germany

[73] Assignee: Degussa-Huls AG, Frankfurt, Germany

[21] Appl. No.: 09/182,196

[22] Filed: Oct. 30, 1998

[30] Foreign Application Priority Data

Oct. 30, 1997 [DE] Germany .......................... 197 47 913

[51] Int. Cl.[7] .................................................. C07C 209/32
[52] U.S. Cl. ............................ 564/448; 564/445; 564/446
[58] Field of Search ..................................... 564/445, 446, 564/448

[56] References Cited

U.S. PATENT DOCUMENTS

| | | |
|---|---|---|
| 5,166,396 | 11/1992 | Hutchmacher . |
| 5,166,444 | 11/1992 | Hutchmacher . |
| 5,283,366 | 2/1994 | Hutchmacher . |
| 5,373,068 | 12/1994 | Piana . |
| 5,504,254 | 4/1996 | Haas . |
| 5,583,260 | 12/1996 | Haas . |
| 5,679,860 | 10/1997 | Haas . |

FOREIGN PATENT DOCUMENTS

| | | |
|---|---|---|
| 0 449 089 B1 | 10/1991 | European Pat. Off. . |
| 0 659 734 A1 | 6/1995 | European Pat. Off. . |
| 0 729 937 A1 | 9/1996 | European Pat. Off. . |
| WO 92/21650 | 12/1992 | WIPO . |

*Primary Examiner*—Samuel Barts
*Attorney, Agent, or Firm*—Pillsbury Madison & Sutro LLP

[57] ABSTRACT

A process for the production of primary and/or secondary amines from imines or nitriles, comprising an aminating hydrogenation of imine or of nitrile with hydrogen in the presence of ammonia, of a hydrogenation catalyst based on cobalt, nickel, ruthenium or mixtures of these metals and of a base, at a temperature within the range of 50° C. to 200° C. and at a pressure within the range of 0.3 to 30 MPa. The yield of amine is increased by the use of a quaternary ammonium hydroxide as base. Preferably a tetraalkylammonium hydroxide is used in a quantity of from 0.01 to 100 mMol per mol of amine or of nitrile. The process is suitable in particular for the production of isophoronediamine from isophorone nitrile imine.

7 Claims, No Drawings

PROCESS FOR THE PRODUCTION OF AMINES FROM IMINES OF NITRILES

FIELD OF THE INVENTION

This invention relates to a process for the production of primary or secondary amines by aminating hydrogenation of an imine or nitrile in the presence of a hydrogenation catalyst, in particular of a catalyst based on one or more of the metals cobalt, nickel and ruthenium, and on a base containing a hydroxyl anion, the base preferably being a quaternary ammonium hydroxide.

The invention relates in particular to a process for the production of isophoronediamine (=3-aminoethyl-3,5,5-trimethylcyclohexylamine) by aminating hydrogenation of isophorone nitrile imine (=3-cyano-3,5,5-trimethylcyclohexaneimine) with hydrogen in the presence of ammonia.

BACKGROUND OF THE INVENTION

Primary or secondary amines can be produced in known manner by catalytic hydrogenation of aldimines or ketimines in the presence of ammonia, generally referred to as aminating hydrogenation. Primary amines are similarly attainable by aminating hydrogenation of nitriles. Suitable hydrogenation catalysts are in particular those based on or more of the metals cobalt, nickel and ruthenium; these catalysts can contain in addition other metals, as a result of the production or as promoters. Increasing the selectivity of the aminating hydrogenation by the presence of an alkali metal hydroxide or alkaline-earth hydroxide is also known.

According to WO 92/21650, dinitriles having high selectivity can be converted into aminonitriles by carrying out the hydrogenation with hydrogen using a Raney nickel or Raney cobalt catalyst in the presence of ammonia and of an organic base, such as LiOH, NaOH or KOH.

The one- or two-step production of isophoronediamine from isophorone nitrile (=3-cyano-3,5,5-trimethylcyclohexanone) is also based on an aminating hydrogenation. In the one-step embodiment, isophorone nitrile is iminated in situ in the presence of ammonia and the isophorone nitrile imine formed is hydrogenated to isophoronediamine—see, for example, EP-A 0 659 734. In the two-step embodiment, in a first step isophorone nitrile is iminated in the presence or absence of an acidic imination catalyst and the reaction mixture containing the isophorone nitrile imine is passed to the hydrogenation step—see, for example, DE-PS 195 40 191, EP-B 0 449 089 and EP-A 0 729 937. As isophoronediamine is a large-scale industrial product, the endeavours of the experts are directed towards obtaining as pure a product as possible in the highest yield possible.

EP-A 0 449 089 discloses a two-step process for the production of isophoronediamine (IPDA) from isophorone nitrile (IPN) wherein, in a first step, IPN is reacted with ammonia on acidic metal oxides to form isophorone nitrile imine and then, in the presence of ammonia and of a hydrogenation catalyst, in particular a catalyst based on cobalt and/or ruthenium, optionally in the presence of basic components such as alkali metal hydroxides or alkaline-earth hydroxides or basic supports, the imine is hydrogenated with hydrogen to form IPDA. In the reworking of the process according to EP-B 0 449 089, in which, however, an organopolysiloxane containing sulfo groups as in DE patent application 196 27 265.3 was used as imination catalyst and the hydrogenation was carried out at 6 MPa instead of at 25 MPa, it was found that with the sole use of a basic cobalt catalyst (90% Co, 5% Mn and 1.9% Na), the yield of isophoronediamine rapidly decreased with increasing operating time—see comparison example 4. It was also ascertained—see comparison examples 5 to 7—that even on continuous addition of an alkali metal hydroxide to the aminating hydrogenation of isophorone nitrile imine, as recommended in EP-A 0 729 937, there is still a considerable formation of secondary products which lead to a decrease in the yield of pure isophoronediamine during the working up of the reaction mixture by distillation.

SUMMARY OF THE INVENTION

The object of the present invention is the provision of a further improved process for the production of primary amines from nitriles and of primary or secondary amines from imines by aminating hydrogenation, in particular for the production of isophorone nitrile imine, in which the improvement is to be seen in a decrease in the formation of secondary products and consequently in an increase in the yield, accompanied by high purity in the amines isolatable from the reaction mixture in the hydrogenation step.

This object is achieved by a process for the production of primary and/or secondary amines from imines or nitriles, in particular for the production of 3-aminomethyl-3,5,5-trimethylcyclohexylamine (isophoronediamine) from 3-cyano-3,5,5-trimethylcyclohexaneimine (isophorone nitrile imine), comprising an aminating hydrogenation of an imine or of a nitrile, in particular of isophorone nitrile imine, with hydrogen in the presence of ammonia, of a hydrogenation catalyst based on cobalt, nickel, ruthenium or mixtures of these metals and of a hydroxide base, at a temperature within the range of 50° C. to 200° C. and at a pressure within the range of 0.3 to 30 MPa and working up of the reaction mixture, which is characterised in that the aminating hydrogenation is carried out in the presence of a quaternary ammonium hydroxide.

Although the problem of secondary product formation and consequently of decrease in yield arises in the aminating hydrogenation of any imine or nitrile, the following statements are directed principally towards the production of isophoronediamine from isophorone nitrile imine, using in particular a reaction mixture containing this imine, resulting from an imination of isophorone nitrile preceding the aminating hydrogenation.

The imines attainable by the process according to the invention may be any aldimines and ketimines of aliphatic, cycloaliphatic and aromatic-aliphatic compounds having one or two imino groups; the nitriles may be any aliphatic, cycloaliphatic, aromatic or heteroaromatic compounds having one or two nitrile groups. Both the imines and the nitriles may contain in addition other functional groups, including those which are themselves amenable to the aminating hydrogenation. They are preferably aliphatic or cycloaliphatic imines and nitriles and also nitrile imines, in particular those having 4 to 12 carbon atoms. An example of the last-named class of substances is the isophorone nitrile imine (=3-cyano-3,5,5-trimethylcyclohexaneimine) obtainable by imination of isophorone nitrile; the invention is explained in detail using this example.

Another preferred class of substances attainable by the process according to the invention comprises aliphatic dinitriles having 4 to 12 C atoms, in particular glutaronitrile, adiponitrile and dodecanedinitrile, which can be converted into the corresponding monoaminonitriles or diamines.

The quaternary ammonium hydroxides to be used are bases corresponding to the general formula $(R^1R^2R^3R^4N)^+$ OH⁻, wherein $R^1$ to $R^4$ can be identical or different and can denote aliphatic, cycloaliphatic or aromatic hydrocarbon groups. $R^1$ to $R^4$ preferably denote aliphatic hydrocarbon groups, in particular those having 1 to 12 C atoms, most particularly 1 to 4 C atoms. $R^1$, $R^2$ and $R^3$ are usefully identical and are each a ($C_1$ to $C_4$)-alkyl, and $R^4$ is ($C_1$ to $C_{18}$)-alkyl or aryl; examples are phenyl or lauryl trimethylammonium hydroxide. Tetraalkylammonium hydroxides are particularly preferred, in particular those selected from among tetramethyl-, tetraethyl-, tetra-n-propyl- and tetra-n-butylammonium hydroxide.

The hydrogenation is suitably carried out in the presence of from 0.01 to 100 mMol, in particular from 0.05 to 50 mMol and particularly preferably from 0.2 to 20 mMol, of a tetraalkylammonium hydroxide, each based on one mol of imine or nitrile.

The process according to the invention can be carried out batchwise or continuously. In the continuous technique, hydrogen and in addition a quaternary ammonium hydroxide, besides the imine, ammonia and optionally a solvent, or a reaction mixture containing these substances, are passed continuously from a preceding imination step to the reactor containing a suspension catalyst or fixed-bed catalyst. The ammonium hydroxide base can be passed as pure substance or as solution to the reactor, or optionally even to the reaction mixture from the imination step. The use of a fixed-bed catalyst operated by the trickle bed technique is particularly preferred.

Suitable catalysts are in particular those wherein the metals active in the hydrogenation are selected from among cobalt, nickel, iron and ruthenium and other precious metals or mixtures of such metals. The use of catalysts based on Co, Ni and/or Ru is preferred. In addition, the catalyst may contain other metals from the production of, for instance, aluminium, zinc or silicon, which, during the production of Raney catalysts, were present in the form of leachable alloying components in a Raney alloy. The catalyst may moreover contain conventional promoters, for example, those from among Cr, Fe, Co, Mn, Ta, Mo and Ti.

Suitable catalysts are, for example, Raney catalysts, full contacts or supported contacts, for instance, Co, Ni and/or Ru on oxides, such as $Al_2O_3$, $TiO_2$, $ZrO_2$, ZnO, $MgO/Al_2O_3$, which are mentioned in the cited prior art documents. Shaped metal fixed-bed Raney catalysts, obtainable by the process described in the DE patent application 197 21 897, are also particularly preferred.

The aminating hydrogenation is carried out in the presence of ammonia, wherein 2 or more mol $NH_3$, preferably 5 to 500 mol $NH_3$, are conventionally used per mol of imine or nitrile. Besides being used for the amination, ammonia serves partly or wholly as a solvent.

The hydrogenation can be carried out in the presence or absence of organic solvents resistant to hydrogenation. The use of a water-soluble alcohol is particularly useful, in particular a lower alcohol having 1 to 4 C atoms, preferably methanol, or a water-soluble ether, such as tetrahydrofuran. Glycols are also suitable as solvents, provided that their boiling point is sufficiently far from that of the reaction products of the aminating hydrogenation.

The aminating hydrogenation is suitably carried out at low to moderate pressure, for instance, 0.3 to 10 MPa, but can also take place at high pressure, that is, within the range of above 10 to 30 MPa. The temperature during the hydrogenation is suitably within the range of about 50° C. to 250° C., in particular 50° C. to 150° C., but it can also be outside the above-mentioned limits. In many cases it may be useful to raise the temperature continuously or gradually during the hydrogenation. In the continuous mode of operation, hydrogen can be introduced cocurrent or countercurrent to the reaction mixture containing the imine. The hydrogenation can be carried out in a trickle bed technique or sump technique in a single reactor or in several reactors connected together, preferably in series.

In the production of isophoronediamine, preferably a reaction mixture containing isophorone nitrile imine is passed to the aminating hydrogenation. The above-mentioned mixture can be that obtained immediately in the imination of isophorone nitrile with ammonia in the presence or absence of an organic solvent, such as methanol in particular, in the presence or absence of an acidic imination catalyst, or that obtained from such a reaction mixture after addition or distillation off of solvents and/or of a portion of the ammonia. The above-mentioned imination is carried out preferably in the presence of an imination catalyst, such as an acidic metal oxide, an acidic zeolite or an acidic ion exchanger, for instance, an organopolysiloxane containing sulfo groups as in DE patent application 196 27 265.3. Owing to the presence of a lower alcohol such as, for example, methanol, it is possible to carry out aminating hydrogenation at lower pressure than is possible in the absence of the above-mentioned alcohol.

This application is based on priority application DE 19747913.8, filed Oct. 30, 1997, which entire disclosure is incorporated herein by reference.

DETAILED DESCRIPTION OF THE PREFERRED EMBODIMENTS

It follows from the Examples and Comparison Examples described below that, surprisingly, the yield of pure isophoronediamine is successfully increased by several percentile points by using a quaternary ammonium hydroxide instead of an alkali metal hydroxide or alkaline-earth hydroxide.

EXAMPLES

Isophoronediamine was produced by imination of isophorone nitrile in the presence of an imination catalyst and methanol as solvent (=first step) and aminating hydrogenation of the reaction mixture from the first step (=second step). The reaction mixture from the second step was analysed by gas chromatography to determine its composition and worked up by distillation.

In the imination of all Examples and Comparison Examples, an organopolysiloxane containing sulfo groups was used as imination catalyst (see DE 196 27 265.3). The catalyst was arranged as a fixed bed in a reactor tube (internal diameter 20 mm, length 250 mm, catalyst loading 30 ml). The imination reactor was operated at 35° C. by the sump technique. The solution introduced consisted of 15 wt. % isophorone nitrile, 30 wt. % ammonia and 55 wt. % methanol. This solution was passed through the imination reactor from bottom to top at a mass flow rate of 80 ml/h.

The reaction mixture from the first step was introduced from the top into the hydrogenation reactor equipped with a fixed-bed catalyst (internal diameter 17 mm, length 350 mm, loading 150 ml of catalyst) (trickle bed technique). The base was introduced into the reaction mixture immediately before the hydrogenation reactor. The hydrogen was passed into the reactor from the top at a volumetric flow rate of 36 l/h. The hydrogenation was carried out at 100° C. and at a pressure of 6 MPa. The product mixture from the second reactor was collected in a receiver and worked up in the conventional manner. The hydrogenation catalysts used were:

C1: shaped Raney Co fixed-bed catalyst, produced and activated as described in Example 1 of DE 197 21 897.0

C2: shaped Co fixed-bed catalyst according to EP-A 0 648 534—see also Comparison Example 1 in DE 197 21 897.0 cited above C3: commercial cobalt supported catalyst (Co on a silicate)

C4: reduced Co catalyst containing 90% Co, 5% Mn and 1.9% Na in the form of 4 mm strands (catalyst similar to the catalyst used in the process of EP-A 0 449 089).

Details regarding C1, C2 and C3 may be seen in Table 1.

TABLE 1

| Dimensions | C1<br>5 ø × 5 | C2<br>5 ø × 5 | C3<br>4.5 ø × 5 |
| --- | --- | --- | --- |
| Cobalt (wt. %) | 60 | 60 | 45 |
| Aluminium (wt. %) | 40 | 40 | — |
| Bulk density (kg/l) | 1.2 | 2.2 | 0.74 |
| Pore volume (cm$^3$/g) | 0.3 | 0.05 | 0.3 |
| Shell thickness (mm) | 0.8 | 0.3 | n.a. |
| Fracture strength (N) | 120 | 300 | 80 |

NaOH or tetramethylammonium hydroxide (TMAH) was used as base, each in a quantity of 5 mMol base per mol of the isophorone nitrile used in the first step. No base was used in the Comparison Examples 1 to 4.

Table 2 contains data on the yield of isophoronediamine (determined by gas chromatography) and on the purity of the isophoronediamine obtained from the distillation of the reaction mixture in the Examples (Ex 1 to Ex 3) and Comparison Examples Cmp Ex 1 to Cmp Ex 7.

TABLE 2

| No. | Catalyst | Base | Yield | Purity |
| --- | --- | --- | --- | --- |
| Cmp Ex 1 | C1 | — | 89.7 | 99.9 |
| Cmp Ex 2 | C2 | — | 89.1 | 99.75 |
| Cmp Ex 3 | C3 | — | 84.3 | 99.85 |
| Cmp Ex 4 | C4 | Na$_2$O in the catalyst | 87.6*)<br>84.5**) | |
| Ex 1 | C1 | TMAH | 95.7 | 99.9 |
| Cmp Ex 1 | C1 | NaOH | 92.4 | 99.9 |
| Ex 2 | C2 | TMAH | 95 | 99.75 |
| Cmp Ex 2 | C2 | NaOH | 92.1 | 99.75 |
| Ex 3 | C3 | TMAH | 90.2 | 99.75 |
| Cmp Ex 3 | C3 | NaOH | 87.9 | 99.7 |

*)after 21 h operation
**)after 91 h operation

The experiments show the increase in yield when NaOH is exchanged for TMAH. The effect is apparent with different catalysts. An Na-containing catalyst (C4) has an inadequate useful life.

What is claimed is:

1. A process for the production of at least one of primary amines and secondary amines from imines or nitriles comprising:

aminating hydrogenation of an imine or a nitrile with hydrogen in the presence of (a) ammonia, (b) a hydrogenation catalyst based on cobalt, nickel, ruthenium or mixtures of these metals and (c) a hydroxide base comprising a quaternary ammonium hydroxide, at a temperature within the range of 50° C. to 250° C. and at a pressure within the range of 0.3 to 30 Mpa; and working up of the reaction mixture.

2. The process according to claim 1, wherein the quaternary ammonium hydroxide comprises a tetra-alkyl ammonium hydroxide selected from the group consisting of tetramethyl-, tetraethyl-, tetra-n-propyl- and tetra-n-butylammonium hydroxide.

3. The process according to claim 1, wherein the hydroxide base comprises from 0.05 to 50 mMol tetraalkylammonium hydroxide per mol of imine or nitrile.

4. The process according to claim 1, for the production of isophoronediamine comprising:

aminating hydrogenation of isophorone nitrile imine, in one or more steps, in the presence of from 0.02 to 20 mMol of a quaternary ammonium hydroxide per mol of isophorone nitrile imine, optionally in the presence of an organic solvent at a temperature within the range of 50° C. to 150° C.

5. The process according to claim 4 wherein the quaternary ammonium hydroxide comprises a tetra (C$_1$- to C$_4$-) alkylammonium hydroxide.

6. The process according to claim 4, wherein the aminating hydrogenation is carried out in a fixed-bed reactor or suspension reactor comprising, continuously passing through the reactor a reaction mixture containing isophorone nitrile imine, obtained by imination of isophorone nitrile in the presence of an excess of ammonia, optionally in the presence of an acidic imination catalyst and optionally in the presence of an organic solvent, and a quaternary ammonium hydroxide, and working up the mixture leaving the reactor by distillation.

7. The process according to claim 4 wherein the aminating hydrogenation is carried out in a fixed-bed reactor by a trickle bed technique, comprising:

passing the reaction mixture to be aminated by hydrogenation through the reactor in one or several temperature steps arranged in order of increasing temperature.

* * * * *